United States Patent
Thompson

(10) Patent No.: US 12,281,306 B1
(45) Date of Patent: Apr. 22, 2025

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

(*) Notice: Subject to any disclaimer, the term of this patent is extended or adjusted under 35 U.S.C. 154(b) by 0 days.

(21) Appl. No.: 18/745,792

(22) Filed: Jun. 17, 2024

(51) Int. Cl.
*C12N 15/113* (2010.01)
*C12N 15/86* (2006.01)

(52) U.S. Cl.
CPC ............ *C12N 15/113* (2013.01); *C12N 15/86* (2013.01); *C12N 2310/141* (2013.01); *C12N 2750/14143* (2013.01)

(58) Field of Classification Search
CPC . C12N 15/113; C12N 15/86; C12N 2310/141
See application file for complete search history.

(56) References Cited

PUBLICATIONS

Bronisz et al. Reprogramming of the tumour microenvironment by stromal PTEN-regulated miR-320. Nature Cell Biology 14: 159-167. (Year: 2012).*

Han et al. lncRNA DLEU2 promotes gastric cancer progression through ETS2 via targeting miR-30a-5p. Cancer Cell Int 21: 1-11. ( Year: 2021).*

Hong et al. A genetic variation in microRNA target site of ETS2 is associated with clinical outcomes of paclitaxel-cisplatin hemotherapy in non-small cell lung cancer. Oncotarget 7: 15948-15958. (Year: 2016).*

Qiao et al. microRNA-145-5p attenuates acute lung injury via targeting ETS2. Kaohsiung J Med Sci. 38: 565-573. (Year: 2022).*

* cited by examiner

*Primary Examiner* — Arthur S Leonard
*Assistant Examiner* — Keenan A Bates
(74) *Attorney, Agent, or Firm* — Gowling WLG (Canada) LLP

(57) ABSTRACT

The embodiments of the present disclosure relate to one or more compositions or methods that upregulate the production of one or more sequences of micro interfering ribonucleic acid (miRNA). The sequences of miRNA may be complimentary to a sequence of target messenger RNA (mRNA) that encodes for translation of a target biomolecule, such as ETS2. The miRNA can cause the target mRNA to be degraded or inactivated, thereby causing a decrease in bioavailability of the target biomolecule because it is degraded or inactivated by the miRNA. Decreasing the bioavailability of the target biomolecule within a subject that is administered the one or more compositions may address the afflictions experienced by the subject due to overexpression of the target biomolecule.

6 Claims, No Drawings

Specification includes a Sequence Listing.

SEQUENCE LISTING

```
Sequence total quantity: 3
SEQ ID NO: 1           moltype = DNA  length = 5800
FEATURE                Location/Qualifiers
source                 1..5800
                       mol_type = other DNA
                       organism = synthetic construct
SEQUENCE: 1
taatcaacct ctggattaca aaatttgtga aagattgact ggtattctta actatgttgc  60
tccttttacg ctatgtggat acgctgcttt aatgcctttg tatcatgcta ttgcttcccg  120
tatggctttc attttctcct ccttgtataa atcctggttg ctgtctcttt atgaggagtt  180
gtggcccgtt gtcaggcaac gtggcgtggt gtgcactgtg tttgctgacg caaccccac   240
tggttggggc attgccacca cctgtcagct cctttccggg actttcgctt tccccctccc  300
tattgccacg gcggaactca tcgccgcctg ccttgccgc  tgctggacag gggctcggct   360
gttgggcact gacaattccg tggtgttgtc ggggaaatca tcgtcctttc cttggctgct  420
cgcctgtgtt gccacctgga ttctgcgcgg gacgtccttc tgctacgtcc cttcggccct  480
caatccagcg gaccttcctt cccgcggcct gctgccggct ctgcggcctc ttccgcgtct  540
tcgccttcgc cctcagacga gtcggatctc cctttgggcc gcctccccgc ctaagcttat  600
cgataccgtc gagatctaac ttgtttattg cagcttataa tggttacaaa taaagcaata  660
gcatcacaaa tttcacaaat aaagcatttt tttcactgca ttctagttgt ggtttgtcca  720
aactcatcaa tgtatcttat catgtctgga tctcgacctc gactagagca tggctacgta  780
gataagtagc atggcgggtt aatcattaac tacaaggaac ccctagtgat ggagttggcc  840
actccctctc tgcgcgctcg ctcgctcact gaggccgggc gaccaaaggt cgcccgacgc  900
ccgggctttg cccgggcggc ctcagtgagc gagcgagcgc gcagctggcg taatagcgaa  960
gaggcccgca ccgatcgccc ttcccaacag ttgcgcagcc tgaatggcga atggcgattc 1020
```

```
cgttgcaatg gctggcggta atattgttct ggatattacc agcaaggccg atagtttgag   1080
ttcttctact caggcaagtg atgttattac taatcaaaga agtattgcga caacggttaa   1140
tttgcgtgat ggacagactc ttttactcgg tggcctcact gattataaaa acacttctca   1200
ggattctggc gtaccgttcc tgtctaaaat ccctttaatc ggcctcctgt ttagctcccg   1260
ctctgattct aacgaggaaa gcacgttata cgtgctcgtc aaagcaacca tagtacgcgc   1320
cctgtagcgg cgcattaagc gcggcgggtg tggtggttac gcgcagcgtg accgctacac   1380
ttgccagcgc cctagcgccc gctcctttcg ctttcttccc ttcctttctc gccacgttcg   1440
ccggctttcc ccgtcaagct ctaaatcggg gctccctttt agggttccga tttagtgctt   1500
tacggcacct cgaccccaaa aaacttgatt agggtgatgg ttcacgtagt gggcatcgc   1560
cctgatagac ggttttttcgc cctttgacgt tggagtccac gttctttaat agtggactct   1620
tgttccaaac tggaacaaca ctcaaccccta tctcggtcta ttcttttgat ttataaggga   1680
ttttgccgat ttcggcctat tggttaaaaa atgagctgat ttaacaaaaa tttaacgcga   1740
attttaacaa aatattaacg tttacaattt aaatatttgc ttatacaatc ttcctgtttt   1800
tggggctttt ctgattatca accggggtac atatgattga catgctagtt ttacgattac   1860
cgttcatcga ttctcttgtt tgctccagac tctcaggcaa tgacctgata gcctttgtag   1920
agacctctca aaaatagcta ccctctccgg catgaattta tcagctagaa cggttgaata   1980
tcatattgat ggtgatttga ctgtctccgg cctttctcac ccgtttgaat ctttacctac   2040
acattactca ggcattgcat ttaaaatata tgagggttct aaaaattttt atccttgcgt   2100
tgaaataaag gcttctcccg caaaagtatt acagggtcat aatgtttttg gtacaaccga   2160
tttagcttta tgctctgagg ctttattgct taattttgct aattctttgc cttgcctgta   2220
tgatttattg gatgttggaa ttcctgatgc ggtattttct ccttacgcat ctgtgcggta   2280
tttcacaccg catatggtgc actctcagta caatctgctc tgatgccgca tagttaagcc   2340
agccccgaca cccgccaaca cccgctgacg cgccctgacg ggcttgtctg ctcccggcat   2400
ccgcttacag acaagctgtg accgtctccg ggagctgcat gtgtcagagg ttttcaccgt   2460
catcaccgaa acgcgcgaga cgaaagggcc tcgtgatacg cctatttttta taggttaatg   2520
tcatgataat aatggtttct tagacgtcag gtggcacttt tcggggaaat gtgcgcggaa   2580
cccctatttg tttatttttc taaatacatt caaatatgta tccgctcatg agacaataac   2640
cctgataaat gcttcaataa tattgaaaaa ggaagagtat gagtattcaa catttccgtg   2700
tcgcccttat tcccttttttt gcggcatttt gccttcctgt ttttgctcac ccagaaacgc   2760
tggtgaaagt aaaagatgct gaagatcagt tgggtgcacg agtgggttac atcgaactgg   2820
atctcaacag cggtaagatc cttgagagtt ttcgccccga agaacgtttt ccaatgatga   2880
gcactttaa agttctgcta tgtggcgcgg tattatcccg tattgacgcc gggcaagagc   2940
aactcggtcg ccgcatacac tattctcaga atgacttggt tgagtactca ccagtcacag   3000
aaaagcatct tacggatggc atgacagtaa gagaattatg cagtgctgcc ataaccatga   3060
gtgataacac tgcggccaac ttacttctga caacgatcga aggaccgaag gagctaaccg   3120
cttttttgca acatgggg gatcatgtaa ctcgccttga tcgttgggaa ccggagctga   3180
atgaagccat accaaacgac gagcgtgaca ccacgatgcc tgtagcaatg gcaacaacgt   3240
tgcgcaaact attaactggc gaactactta ctctagcttc ccggcaacaa ttaatagact   3300
ggatggaggc ggataaagtt gcaggaccac ttctgcgctc ggcccttccg gctggctggt   3360
ttattgctga taaatctgga gccggtgagc gtgggtctcg cggtatcatt gcagcactgg   3420
ggccagatgg taagccctcc cgtatcgtag ttatctacac gacggggagt caggcaacta   3480
tggatgaacg aaatagacag atcgctgaga taggtgcctc actgattaag cattggtaac   3540
tgtcagacca agtttactca tatatacttt agattgattt aaaacttcat ttttaattta   3600
aaaggatcta ggtgaagatc ctttttgata atctcatgac caaaatccct taacgtgagt   3660
tttcgttcca ctgagcgtca gaccccgtag aaaagatcaa aggatcttct tgagatcctt   3720
ttttttctgcg cgtaatctgc tgcttgcaaa caaaaaaacc accgctacca gcggtggttt   3780
gtttgccgga tcaagagcta ccaactcttt tccgaaggt aactggcttc agcagagcgc   3840
agataccaaa tactgtcctt ctagtgtagc cgtagttagg ccaccacttc aagaactctg   3900
tagcaccgcc tacatacctc gctctgctaa tcctgttacc agtggctgct gccagtggcg   3960
ataagtcgtg tcttaccggg ttggactcaa gacgatagtt accggataag gcgcagcggt   4020
cgggctgaac ggggggttcg tgcacacagc ccagcttgga gcgaacgacc tacaccgaac   4080
tgagatacct acagcgtgag ctatgagaaa gcgccacgct tcccgaaggg agaaaggcgg   4140
acaggtatcc ggtaagcggc agggtcggaa caggagagcg cacgagggag cttccagggg   4200
gaaacgcctg gtatctttat agtcctgtcg ggtttcgcca cctctgactt gagcgtcgat   4260
ttttgtgatg ctcgtcaggg gggcggagcc tatggaaaaa cgccagcaac gcggcctttt   4320
tacggttcct ggccttttgc tggccttttt gctcacatgt tctttcctgcg ttatcccctg   4380
attctgtgga taaccgtatt accgcctttg agtgagctga taccgctcgc cgcagccgaa   4440
cgaccgagcg cagcgagtca gtgagcgagg aagcggaaga gcgcccaata cgcaaaccgc   4500
ctctccccgc gcgttggccg attcattaat gcagcagctg cgcgctcgct cgctcactga   4560
ggccgcccgg gcaaagcccg gcgtcgggc gacctttggt cgcccggcct cagtgagcga   4620
gcgagcgcgc agagagggag tggccaactc catcactagg ggttccttgt agttaatgat   4680
taacccgcca tgctacttat ctacgtagcc atgctctagg acattgatta ttgactagtg   4740
gagttccgcg ttacataact tacggtaaat ggcccgcctg gctgaccgcc caacgacccc   4800
cgcccattga cgtcaataat gacgtatgtt cccatagtaa caataggactttccat   4860
tgacgtcaat gggtggagta tttacggtaa actgcccact tggcagtaca tcaagtgtat   4920
catatgccaa gtacgccccc tattgacgtc aatgacggta aatggcccgc ctggcattat   4980
gcccagtaca tgaccttatg gactttcct acttggcagt acatctacgt attagtcatc   5040
gctattacca tggtcgaggt gagccccacg ttctgcttca ctctccccat ctccccccc   5100
tccccacccc caattttgta tttatttatt ttttaattat tttgtgcagc gatgggggcg   5160
ggggggggg ggggcgcgcg ccaggcgggg cggggcgggg cgaggggcgg ggcggggcga   5220
ggcggagagg tgcggcggca gccaatcaga gcggcgcgct ccgaaagttt ccttttatgg   5280
cgaggcggcg gcggcggcgg ccctataaaa agcgaagcgc gcggcgggcg ggagtcgctg   5340
cgcgctgcct tcgccccgtg ccccgctccg ccgccgcctc gcgccgcccg ccccggctct   5400
gactgaccgc gttactaaaa cagtcaagct cggccccgcg gtttgcccgg gcggcctccc   5460
gcgggcgccc cctcctcac ggcgagcgct gccacgtcag acgaagggcg cagcgagcgt   5520
cctgatcctt ccgcccggac gctcaggaca gcggcccgct gctcataaga ctcggcctta   5580
gaaccccagt atcagcagaa ggacatttta ggacgggact tgggtgactc tagggcactg   5640
gttttctttc cagagagcgg aacaggcgag gaaaagtagt cccttctcgg cgattctgcg   5700
gagggatctc cgtggggcgg tgaacgccga tgatgcctct actaaccatg ttcatgtttt   5760
```

```
cttttttttt ctacaggtcc tgggtgacga acagggtacc            5800

SEQ ID NO: 2           moltype = DNA  length = 539
FEATURE                Location/Qualifiers
source                 1..539
                       mol_type = other DNA
                       organism = synthetic construct
SEQUENCE: 2
gccaccatgg ccaccggctc tcgcacaagc ctgctgctgg cttttcggact gctgtgcctg   60
ccttggctcc aggagggctc cgccgctagc atcgataccg tcgctatgtg ctggaggctt  120
gctgaaggct gtatgctggg catgcagact gccagaacta tgttttggcc tctgactgac  180
ggcatgcaga cccagaacta tcaggacaca aggcctgtta ctagcactca catgaacaa   240
atggcctcta gcctggaggc ttgctgaagg ctgtatgctg tttaaattcc catagccatc  300
gccgttttgg cctctgactg acggcgatgg ctgggaattt aaacaggaca caaggcctgt  360
tactagcact cacatggaac aaatggcctc tagcctggag gcttgctgaa ggctgtatgc  420
tgacatctga aataatcctg ttcgcgtttt ggcctctgac tgacgcgaac aggaatttca  480
gatgtcagga cacaaggcct gttactagca ctcacatgga acaaatggcc tctctagaa   539

SEQ ID NO: 3           moltype = DNA  length = 6339
FEATURE                Location/Qualifiers
source                 1..6339
                       mol_type = other DNA
                       organism = synthetic construct
SEQUENCE: 3
taatcaacct ctggattaca aaatttgtga aagattgact ggtattctta actatgttgc   60
tccttttacg ctatgtggat acgctgcttt aatgcctttg tatcatgcta ttgcttcccg  120
tatggctttc attttctcct ccttgtataa atcctggttg ctgtctcttt atgaggagtt  180
gtggcccgtt gtcaggcaac gtggcgtggt gtgcactgtg tttgctgacg caaccccac   240
tggttggggc attgccacca cctgtcagct cctttccggg actttcgctt tcccctccc   300
tattgccacg gcggaactca tcgccgcctg ccttgcccgc tgctggacag gggctcggt   360
gttgggcact gacaattccg tggtgttgtc ggggaaatca tcgtcctttc cttggctgct  420
cgcctgtgtt gccacctgga ttctgcgcgg gacgtcctcc tgctacgtcc cttcggccct  480
caatccagcg gaccttcctt cccgcggcct gctgccggct ctgcgcctc ttccgcgtct   540
tcgccttcgc cctcagacga gtcggatctc cctttgggcc gcctccccgc ctaagcttat  600
cgataccgtc gagatctaac ttgtttattg cagcttataa tggttacaaa taaagcaata  660
gcatcacaaa tttcacaaat aaagcatttt tttcactgca ttctagttgt ggtttgtcca  720
aactcatcaa tgtatcttat catgtctgga tctcgacctc gactagagca tggctacgta  780
gataagtagc atggcgggtt aatcattaac tacaaggaac cctagtgat ggagttggcc    840
actccctctc tgcgcgctcg ctcgctcact gaggccgggc gaccaaaggt cgcccgacgc  900
ccgggctttg cccgggcggc ctcagtgagc gagcgagcgc gcagctggcg taatagcgaa  960
gaggcccgca ccgatcgccc ttcccaacag ttgcgcagcc tgaatggcga atggcgattc 1020
cgttgcaatg gctggcggta atattgttct ggatattacc agcaaggccg atagtttgag 1080
ttcttctact caggcaagtg atgttattac taatcaaaga atgattgcga acggttaa   1140
tttgcgtgat ggacagactc ttttactcgg tggcctcact gattataaaa acacttctca 1200
ggattctggc gtaccgttcc tgtctaaaat ccctttaatc ggcctcctgt ttagctcccg 1260
ctctgattct aacgaggaaa gcacgttata cgtgctcgtc aaagcaacca tagtacgcgc 1320
cctgtagcgg cgcattaagc gcggcgggtg tggtggttac gcgcagcgtg accgctacac 1380
ttgccagcgc cctagcgccc gctccttcg ctttcttccc ttcctttctc gccacgttc    1440
ccggctttcc ccgtcaagct ctaaatcggg ggctccctt agggttccga tttagtgctt  1500
tacggcacct cgaccccaaa aaacttgatt agggtgatgg ttcacgtagt gggccatcgc 1560
cctgatagac ggttttttcgc cctttgacgt tggagtccac gttctttaat agtggactct 1620
tgttccaaac tggaacaaca ctcaacccta tctcggtcta ttcttttgat ttataaggga 1680
ttttgccgat ttcggcctat tggttaaaaa atgagctgat ttaacaaaaa tttaacgcga 1740
attttaacaa aatattaacg tttacaattt aaatatttgc ttatacaatc ttcctgtttt 1800
tggggctttt ctgattatca accggggtac atatgattga catgctagtt ttacgattac 1860
cgttcatcga ttctcttgtt tgctccagac tctcaggcaa tgacctgata gcctttgtag 1920
agacctctca aaaatagcta cccctctccg catgaattta tcagctagaa cggttgaata 1980
tcatattgat ggtgatttga ctgtctccgg cctttctcac ccgtttgaat ctttacctac 2040
acattactca ggcattgcat ttaaaatata tgagggttcc aaaaaattttt atccttgcgt 2100
tgaaataaag gcttctcccg caaaagtatt acagggtcat aatgttttg gtacaaccga 2160
tttagcttta tgctctgagg cttattgct taatttgct aattcttgc cttgcctgta    2220
tgatttattg gatgttggaa ttcctgatgc ggtattttct ccttacgcat ctgtgcggta 2280
tttcacaccg catatggtgc actctcagta caatctgctc tgatgccgca tagttaagcc 2340
agccccgaca cccgccaaca cccgctgacg cgccctgacg gcttgtctg ctcccggcat  2400
ccgcttacag acaagctgtg accgtctccg ggagctgcat gtgtcagagg ttttcaccgt 2460
catcaccgaa acgcgcgaga cgaaagggcc tcgtgatacg cctattttta taggttaatg 2520
tcatgataat aatggtttct tagacgtcag gtggcacttt tcggggaaat gtgcgcggaa 2580
cccctatttg tttatttttc taaatacatt caaatatgta tccgctcatg agacaataac 2640
cctgataaat gcttcaataa tattgaaaaa ggaagagtat gagtattcaa catttccgtg 2700
tcgcccttat tcccttttt gcggcatttt gccttcctgt ttttgctcac ccagaaacgc 2760
tggtgaaagt aaaagatgct gaagatcagt tgggtgcacg agtgggttac atcgaactgg 2820
atctcaacag cggtaagatc cttgagagtt ttcgccccga agaacgtttt ccaatgatga 2880
gcacttttaa agttctgcta tgtggcgcgg tattatcccg tattgacgcc gggcaagagc 2940
aactcggtcg ccgcatacac tattctcaga atgacttggt tgagtactca ccagtcacag 3000
aaaagcatct tacgatggca tgacagtaaa gagaattatg cagtgctgcc ataaccatga 3060
gtgataacac tgcggccaac ttacttctga caacgatcgg aggaccgaag gagctaaccg 3120
cttttttgca acaactgggg gatcatgtaa ctcgccttga tcgttgggaa ccggagctga 3180
atgaagccat accaaacgac gagcgtgaca ccacgatgcc tgtagcaatg gcaacaacgt 3240
tgcgcaaact attaactggc gaactactta ctctagcttc ccggcaacaa ttaatagact 3300
```

-continued

```
ggatggaggc ggataaagtt gcaggaccac ttctgcgctc ggcccttccg gctggctggt    3360
ttattgctga taaatctgga gccggtgagc gtgggtctcg cggtatcatt gcagcactgg    3420
ggccagatgg taagccctcc cgtatcgtag ttatctacac gacggggagt caggcaacta    3480
tggatgaacg aaatagacag atcgctgaga taggtgcctc actgattaag cattggtaac    3540
tgtcagacca agtttactca tatatacttt agattgattt aaaacttcat tttttaattta   3600
aaaggatcta ggtgaagatc cttttttgata atctcatgac caaaatccct taacgtgagt   3660
tttcgttcca ctgagcgtca gacccgtag aaaagatcaa aggatcttct tgagatcctt     3720
tttttctgcg cgtaatctgc tgcttgcaaa caaaaaaacc accgctacca gcggtggttt    3780
gtttgccgga tcaagagcta ccaactcttt ttccgaaggt aactggcttc agcagagcgc    3840
agataccaaa tactgtcctt ctagtgtagc cgtagttagg ccaccacttc aagaactctg    3900
tagcaccgcc tacataccta gctctgctaa tcctgttacc agtggctgct gccagtggcg    3960
ataagtcgtg tcttaccggg ttggactcaa gacgatagtt accggataag gcgcagcggt    4020
cgggctgaac ggggggttcg tgcacacagc ccagcttgga gcgaacgacc tacaccgaac    4080
tgagatacct acagcgtgag ctatgagaaa gcgccacgct tcccgaaggg agaaaggcgg    4140
acaggtatcc ggtaagcggc agggtcggaa caggagagcg cacgagggag cttccagggg    4200
gaaacgcctg gtatctttat agtcctgtcg ggtttcgcca cctctgactt gagcgtcgat    4260
ttttgtgatg ctcgtcaggg gggcggagcc tatggaaaaa cgccagcaac gcggcctttt    4320
tacggttcct ggccttttgc tggccttttg ctcacatgtt ctttcctgcg ttatcccctg    4380
attctgtgga taaccgtatt accgcctttg agtgagctga taccgctcgc cgcagccgaa    4440
cgaccgagcg cagcgagtca gtgagcgagg aagcggaaga gcgcccaata cgcaaaccgc    4500
ctctccccgc gcgttggccg attcattaat gcagcagctg cgcgctcgct cgctcactga    4560
ggccgcccca gcaaagcccg ggcgtcgggc gacctttggt cgcccggcct cagtgagcga    4620
gcgagcgcgc agagagggag tggccaactc catcactagg ggttccttgt agttaatgat    4680
taacccgcca tgctacttat ctacgtagcc atgctctagg acattgatta ttgactagtg    4740
gagttccgcg ttacataact tacggtaaat ggcccgcctg gctgaccgcc caacgacccc    4800
cgcccattga cgtcaataat gacgtatgtt cccatagtaa ggacttttccat             4860
tgacgtcaat gggtggagta tttacggtaa actgcccact tggcagtaca tcaagtgtat    4920
catatgccaa gtacgccccc tattgacgtc aatgacggta aatggcccgc ctggcattat    4980
gcccagtaca tgaccttatg ggactttcct acttggcagt acatctacgt attagtcatc    5040
gctattacca tggtcgaggt gagccccacg ttctgcttca ctctccccat ctcccccctc    5100
tccccacccc caattttgta tttatttatt ttttaattat tttgtgcagc gatggggggcg   5160
gggggggggg gggcgcgcg ccaggcgggg cggggcgggg cgaggggcgg ggcggggcga     5220
ggcggagagg tgcggcggca gccaatcaga gcggcgcgct ccgaaagttt cctttatgg     5280
cgaggcggcg gcggcggcgg ccctataaaa agcgaagcgc gcggcgggcg ggagtcgctg    5340
cgcgctgcct tcgccccgtg ccccgctccg ccgccgccgc gcgccgcccg ccccggctct    5400
gactgaccgc gttactaaaa caggtaagtc cggcctccgc gccggtttt ggcgcctccc     5460
gcgggcgccc ccctcctcac ggcgagcgct gccacgtcag acgaagggcg cagcgagcgt    5520
cctgatcctt ccgcccggac gctcaggaca gcggcccgct gctcataaga ctcggcctta    5580
gaacccagt atcagcagaa ggacatttta ggacgggact tgggtgactc tagggcactg     5640
gttttctttc cagagagcgg aacaggcgag gaaaagtagt cccttctcgg cgattctgcg    5700
gagggatctc cgtggggcgg tgaacgccga tgatgcctct actaaccatg ttcatgtttt    5760
cttttttttt ctacaggtcc tgggtgacga acagggtacc gccaccatgg ccaccggctc    5820
tcgcacaagc ctgctgctgg ctttcggact gctgtgcctg cctggctcc aggagggctc     5880
cgccgctagc atcgataccg tcgctatgtg ctggaggctt gctgaaggct gtatgctggg    5940
catgcagact gccagaacta tgttttggcc tctgactgac ggcatgcaga cccagaacta    6000
tcaggacaca aggcctgtta ctagcactca catggaacaa atggcctcta gcctggaggc    6060
ttgctgaagg ctgtatgctg tttaaattcc catagccatc gccgttttgg cctctgactg    6120
acggcgatgg ctgggaattt aaacaggaca caaggcctgt tactagcact cacatggaac    6180
aaatggcctc tagcctggag gcttgctgaa ggctgtatgc tgacatctga aataatcctg    6240
ttcgcgtttt ggcctctgac tgacgcgaac aggaatttca gatgtcagga cacaaggcct    6300
gttactagca ctcacatgga acaaatggcc tctctagaa                           6339
```

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "A8149560-SequenceListing.xml" created on 2024-08-23 and having a size of 15,914 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA that will suppress ETS2 overexpression or mis-expression.

BACKGROUND

Bioactive molecules, including checkpoint molecules, are necessary for the homeostatic control of biological systems. When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro interfering ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is ETS2. In some embodiments of the present disclosure, the target biomolecule participates, directly or indirectly, in one or more immune responses.

In some embodiments of the present disclosure the compositions comprise a plasmid of deoxyribonucleic acid (DNA) that includes one or more insert sequences of nucleotides that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of ETS2.

Some embodiments of the present disclosure relate to a method of making a composition/target cell complex. The method comprising a step of administering a RP comprising SEQ ID NO. 1 and SEQ ID NO. 2 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example ETS2. A first approach utilizes gene vectors containing nucleotide sequences for increasing the endogenous production of one or more sequences of miRNA, which are complete or partial sequences and/or combinations thereof, that target and silence the mRNA of ETS2, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to ETS2 that is found within a subject. A biomolecule may be endogenous or exogenous to a subject and when bioavailable the biomolecule may direct or stimulate an immune process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is ETS2. Without being bound by any particular theory, overexpression of ETS2 is understood to be related to increased incidence and/or severity of Crohn's disease and irritable bowel syndrome. As such, silencing the ETS2 protein product may offer a treatment for such afflications.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as ETS2. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as ETS2.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram) of the patient's body mass. In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with an example being ETS2. The RP is comprised of AAV2 inverted terminal repeats (ITRs), a composite CASI promoter, a human growth hormone (HGH) signal peptide followed by a miRNA expression cassette containing up to six different miRNAs targeting ETS2, followed by a Woodchuck Hepatitis Virus post-transcriptional regulatory element (WPRE) and an SV40 polyA signal.

```
SEQ ID NO. 1 (backbone sequence No. 1):
5'
TAATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCAGCTGGCGTAATAGCGAAGAGGCCCGCACCGATCG

CCCTTCCCAACAGTTGCGCAGCCTGAATGGCGAATGGCGATTCCGTTGCAATGGCTG
```

-continued

```
GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT

GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

ATGAATTTATCAGCTAGAACGGTTAATATCATATTGATGGTGATTTGACTGTCTCC

GGCCTTTCTCACCCGTTTGAATCTTTACCTACACATTACTCAGGCATTGCATTTAAAA

TATATGAGGGTTCTAAAAATTTTTATCCTTGCGTTGAAATAAAGGCTTCTCCCGCAA

AAGTATTACAGGGTCATAATGTTTTTGGTACAACCGATTTAGCTTTATGCTCTGAGG

CTTTATTGCTTAATTTTGCTAATTCTTTGCCTTGCCTGTATGATTTATTGGATGTTGGA

ATTCCTGATGCGGTATTTTCTCCTTACGCATCTGTGCGGTATTTCACACCGCATATGG

TGCACTCTCAGTACAATCTGCTCTGATGCCGCATAGTTAAGCCAGCCCCGACACCCG

CCAACACCCGCTGACGCGCCCTGACGGGCTTGTCTGCTCCCGGCATCCGCTTACAGA

CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGAT

CGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACT

ACTTACTCTAGCTTCCCGGCAACAATTAATAGACTGGATGGAGGCGGATAAAGTTGC
```

-continued

```
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGG
AGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGT
CAGTGAGCGAGGAAGCGGAAGAGCGCCCAATACGCAAACCGCCTCTCCCCGCGCGT
TGGCCGATTCATTAATGCAGCAGCTGCGCGCTCGCTCGCTCACTGAGGCCGCCCGGG
CAAAGCCCGGGCGTCGGGCGACCTTTGGTCGCCCGGCCTCAGTGAGCGAGCGAGCG
CGCAGAGAGGGAGTGGCCAACTCCATCACTAGGGGTTCCTTGTAGTTAATGATTAAC
CCGCCATGCTACTTATCTACGTAGCCATGCTCTAGGACATTGATTATTGACTAGTGG
AGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATC
AAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTA
CGTATTAGTCATCGCTATTACCATGGTCGAGGTGAGCCCCACGTTCTGCTTCACTCTC
CCCATCTCCCCCCCCTCCCCACCCCCAATTTTGTATTTATTTATTTTTTAATTATTTTG
TGCAGCGATGGGGGCGGGGGGGGGGGGGCGCGCGCCAGGCGGGGCGGGGCGGG
GCGAGGGGCGGGGCGGGGCGAGGCGGAGAGGTGCGGCGGCAGCCAATCAGAGCGG
CGCGCTCCGAAAGTTTCCTTTTATGGCGAGGCGGCGGCGGCGGCGGCCCTATAAAA
AGCGAAGCGCGCGGCGGGCGGGAGTCGCTGCGCGCTGCCTTCGCCCCGTGCCCCGC
TCCGCCGCCGCCTCGCGCCGCCCGCCCCGGCTCTGACTGACCGCGTTACTAAAACAG
GTAAGTCCGGCCTCCGCGCCGGGTTTTGGCGCCTCCCGCGGGCGCCCCCCTCCTCAC
GGCGAGCGCTGCCACGTCAGACGAAGGGCGCAGCGAGCGTCCTGATCCTTCCGCCC
GGACGCTCAGGACAGCGGCCCGCTGCTCATAAGACTCGGCCTTAGAACCCCAGTAT
CAGCAGAAGGACATTTTAGGACGGGACTTGGGTGACTCTAGGGCACTGGTTTTCTTT
```

-continued

CCAGAGAGCGGAACAGGCGAGGAAAAGTAGTCCCTTCTCGGCGATTCTGCGGAGGG

ATCTCCGTGGGGCGGTGAACGCCGATGATGCCTCTACTAACCATGTTCATGTTTTCTT

TTTTTTTCTACAGGTCCTGGGTGACGAACAGGGTACC

3'

SEQ ID NO. 2 (miRNA expression cassette No. 2 - ETS2 insert):
5'

GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGG

AGGCTTGCTGAAGGCTGTATGCTGGGCATGCAGACTGCCAGAACTATGTTTTGGCCT

CTGACTGACGGCATGCAGACCCAGAACTATCAGGACACAAGGCCTGTTACTAGCAC

TCACATGGAACAAATGGCCTCTAGCCTGGAGGCTTGCTGAAGGCTGTATGCTGTTTA

AATTCCCATAGCCATCGCCGTTTTGGCCTCTGACTGACGGCGATGGCTGGGAATTTA

AACAGGACACAAGGCCTGTTACTAGCACTCACATGGAACAAATGGCCTCTAGCCTG

GAGGCTTGCTGAAGGCTGTATGCTGACATCTGAAATAATCCTGTTCGCGTTTTGGCC

TCTGACTGACGCGAACAGGAATTTCAGATGTCAGGACACAAGGCCTGTTACTAGCA

CTCACATGGAACAAATGGCCTCTCTAGAA

3'

SEQ ID NO: 3 = SEQ ID NO: 1 + SEQ ID NO: 2
5'

TAATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCAGCTGGCGTAATAGCGAAGAGGCCCGCACCGATCG

CCCTTCCCAACAGTTGCGCAGCCTGAATGGCGAATGGCGATTCCGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

```
TGATTCTAACGAGGAAAGCACGTTATACGTGCTCGTCAAAGCAACCATAGTACGCG
CCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGA
TTTAGTGCTTTACGGCACCTCGACCCCAAAAAACTTGATTAGGGTGATGGTTCACGT
AGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTC
TTTTGATTTATAAGGGATTTTGCCGATTTCGGCCTATTGGTTAAAAAATGAGCTGATT
TAACAAAAATTTAACGCGAATTTTAACAAAATATTAACGTTTACAATTTAAATATTT
GCTTATACAATCTTCCTGTTTTTGGGGCTTTTCTGATTATCAACCGGGGTACATATGA
TTGACATGCTAGTTTTACGATTACCGTTCATCGATTCTCTTGTTTGCTCCAGACTCTC
AGGCAATGACCTGATAGCCTTTGTAGAGACCTCTCAAAAATAGCTACCCTCTCCGGC
ATGAATTTATCAGCTAGAACGGTTGAATATCATATTGATGGTGATTTGACTGTCTCC
GGCCTTTCTCACCCGTTTGAATCTTTACCTACACATTACTCAGGCATTGCATTTAAAA
TATATGAGGGTTCTAAAAATTTTTATCCTTGCGTTGAAATAAAGGCTTCTCCCGCAA
AAGTATTACAGGGTCATAATGTTTTTGGTACAACCGATTTAGCTTTATGCTCTGAGG
CTTTATTGCTTAATTTTGCTAATTCTTTGCCTTGCCTGTATGATTTATTGGATGTTGGA
ATTCCTGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACC
CCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACAT
CGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
```

-continued

```
TCTAGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAG

AGCGCAGATACCAAATACTGTCCTTCTAGTGTAGCCGTAGTTAGGCCACCACTTCAA

GAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTAATTATTTTG

TGCAGCGATGGGGGCGGGGGGGGGGGGCGCGCGCCAGGCGGGGGGGCGGG

GCGAGGGGCGGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGCGGTGAACGCCGATGATGCCTCTACTAACCATGTTCATGTTTTCTT

TTTTTTTCTACAGGTCCTGGGTGACGAACAGGGTACCGCCACCATGGCCACCGGCTC

TCGCACAAGCCTGCTGCTGGCTTTCGGACTGCTGTGCCTGCCTTGGCTCCAGGAGGG
```

-continued

```
CTCCGCCGCTAGCATCGATACCGTCGCTATGTGCTGGAGGCTTGCTGAAGGCTGTAT

GCTGGGCATGCAGACTGCCAGAACTATGTTTTGGCCTCTGACTGACGGCATGCAGAC

CCAGAACTATCAGGACACAAGGCCTGTTACTAGCACTCACATGGAACAAATGGCCT

CTAGCCTGGAGGCTTGCTGAAGGCTGTATGCTGTTTAAATTCCCATAGCCATCGCCG

TTTTGGCCTCTGACTGACGGCGATGGCTGGGAATTTAAACAGGACACAAGGCCTGTT

ACTAGCACTCACATGGAACAAATGGCCTCTAGCCTGGAGGCTTGCTGAAGGCTGTAT

GCTGACATCTGAAATAATCCTGTTCGCGTTTTGGCCTCTGACTGACGCGAACAGGAA

TTTCAGATGTCAGGACACAAGGCCTGTTACTAGCACTCACATGGAACAAATGGCCTC

TCTAGAA

3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) with a sequence of nucleotides, wherein the sequence of nucleotides is SEQ ID NO: 2.

2. The composition of claim 1, wherein the sequence of nucleotides is configured to be delivered to a target cell that over-expressed or mis-expressed ETS2, wherein the sequence of nucleotides is encased in a protein coat, a lipid vesicle, or any combination thereof.

3. The composition of claim 1, wherein the sequence of nucleotides is configured to be delivered to a target cell that over-expressed or mis-expressed ETS2, wherein the sequence of nucleotides is encased in a viral vector.

4. The composition of claim 3, wherein the viral vector is one of a double stranded DNA virus, a single stranded DNA virus, a single stranded RNA virus, or a double stranded RNA virus.

5. The composition of claim 3, wherein the viral vector is an adeno-associated virus.

6. A composition that comprises a recombinant protein (RP) with a sequence of nucleotides, wherein the sequence of nucleotides is SEQ ID NO: 3.

\* \* \* \* \*